United States Patent [19]
Dewey et al.

[11] Patent Number: 6,057,368
[45] Date of Patent: May 2, 2000

[54] TREATMENT OF ADDICTION AND ADDICTION-RELATED BEHAVIOR

[75] Inventors: Stephen L. Dewey, Manorville, N.Y.; Jonathan D. Brodie, Cos Cob, Conn.; Charles R. Ashby, Jr., Miller Place, N.Y.

[73] Assignee: Brookhaven Science Associates LLC, Upton, N.Y.

[21] Appl. No.: 09/129,253

[22] Filed: Aug. 5, 1998

[51] Int. Cl.$^7$ ..................................................... A01N 37/12
[52] U.S. Cl. ........................... 514/561; 514/561; 514/810; 514/812; 514/813
[58] Field of Search .................................... 514/561, 810, 514/812, 813

[56] References Cited

U.S. PATENT DOCUMENTS

| | | | |
|---|---|---|---|
| 4,540,582 | 9/1985 | Seiler et al. | 514/561 |
| 4,595,697 | 6/1986 | Seiler et al. | 514/534 |
| 4,621,145 | 11/1986 | Frieben et al. | 548/543 |
| 5,189,064 | 2/1993 | Blum et al. | 514/561 |

OTHER PUBLICATIONS

Morgan et al., "Longterm Cocaine Administration May Alter Specific Gabergic Pathways", *Abstracts Society for Neuroscience*, 23:1942 (1997).

Kushner et al., "Comparison of the Effects of Vigabatrin on Cocaine Self–Administration and Food Reinforcement", *Abstracts Society for Neuroscience*, 23:1942 (1997).

Dewey et al., "GABAergic Attenuation of Cocaine–Induced Dopamine Release and Locomotor Activity", *Synapse*, 25:393–398 (1997).

Morgan et al., "Effects of Pharmacologic Increases in Brain GABA Levels on Cocaine–Induced Changes in Extracellular Dopamine", *Synapse* 28:60–65 (1998).

Kushner et al., "Gamma–vinyl GABA Attenuates Cocaine–Induced Lowering of Brain Stimulation Reward Thresholds", *Psychopharmacology* 133:383–388 (1997).

Porter et al., "Antiepileptic Drugs", *Basic and Clinical Pharmacology*, ed. by Katzung, B.G., Appelton and Lange, Stamford, CT pp. 386–408 (1998).

Takada et al., "Drug Dependence Study on Vigabatrin in Rhesus Monkeys and Rats", *Arzneim.–Forsch.'Drug Res* 47(II), 1087–1092 (1997).

Nisell et al., "Nicotine Dependence, Midbrain Dopamine Systems and Psychiatric Disorders", *Pharmacology & Toxicology* 76:157–162 (1995).

Nisell et al., "Infusion of Nicotine in the Ventral Tegmental Area or the Nucleus Accumbens of the Rat Differentially Affects Accumbal Dopamine Release", *Pharmacology & Toxicology*, 75:348–352 (1994).

Fudala et al., "Pharmacologic Characterization of Nicotine–Induced Conditioned Place Preference", *Pharmacol Biochem Behav* 22(2) 237–241 (1985).

Clarke et al., "Apparent Absence of Nicotine–Induced Conditioned Place Preference in Rats" *Psychopharmacology*, 92: 84–88 (1987).

Clarke et al., " Evidence That Mesolimbic Dopaminergic Activation Underlies the Locomotor Stimulant Action of Nicotine in Rats", *The Journal of Pharmacology and Experimental Therapeutics*, 246:701–708 (1988).

Henningfield et al., "Control of Behavior by Intravenous Nicotine Injections in Human Subjects", *Pharmacology Biochemistry & Behavior*, 19:1021–1026 (1983).

Jarvik et al., "Pharmacological Treatment of Tobacco Dependence", *Pharmacology Biochemistry & Behavior*, 30:279–294 (1988).

Henningfield et al., "Cigarette Smokers Self–Administer Intravenous Nicotine", *Pharmacology Biochemistry & Behavior* 19:887–890 (1983).

Nisell et al., "Systemic Nicotine–Induced Dopamine Release in the Rat Nucleus Accumbens is Regulated by Nicotinic Receptors in the Ventral Tegmental Area", *Synapse* 16:36–44 (1994).

Pontieri et al., "Effects of nicotine on the nucleus accumbens and similarity to those of addictive drugs" *Nature* 382:255–257 (1996).

Di Chiara et al., "Drugs Abused by Humans Preferentially Increase Synaptic Dopamine Concentrations in the Mesolimbic System of Freely Moving Rats", *Proc. Natl. Acad. Sci. USA*, 85:5274–5278 (1988).

Damsma et al., "Lack of Tolerance to Nicotine–Induced Dopamine Release in the Nucleus Accumbens", *European Journal of Pharmacology*, 168:363–368 (1989).

Imperato et al., "Nicotine Preferentially Stimulates Dopamine Release in the Limbic System for Freely Moving Rats" *European Journal of Pharmacology*, 132:337–338 (1986).

Brazell et al., "Acute Administration of Nicotine Increases the In Vivo Extracellular Levels of Dopamine, 3,4–Dihydroxyphenylacetic Acid and Ascorbic Acid Preferentially in the Nucleus Accumbens of the Rat: Comparison with Caudate–Putamen", *Neuropharmacology* 29:1177–1185 (1990).

Horan et al., "Nicotine Produces Conditioned Place Preference in Lewis But Not Fischer 344 Rats", *Synapse* 26:93–94 (1997).

Lepore et al., "Conditioned Place Preference Induced By $\Delta^9$–Tetrahydrocannabinol: Comparison with Cocaine, Morphine, and Food Reward", *Life Sciences*, 56:2073–2080 (1995).

(List continued on next page.)

*Primary Examiner*—Keith D. MacMillan
*Attorney, Agent, or Firm*—Margaret C. Bogosian

[57] ABSTRACT

The present invention provides a highly efficient method for treating substance addiction and for changing addiction-related behavior of a primate suffering from substance addiction. The method includes administering to a primate an effective amount of a pharmaceutical composition including gamma vinylGABA. The present invention also provides a method of treatment of nicotine addiction by treating a patient with an effective amount of a composition including gamma vinylGABA.

7 Claims, 4 Drawing Sheets

OTHER PUBLICATIONS

Sora et al., "Cocaine reward models: conditioned place preference can be established in dopamine– and in serotonin–transporter knockout mice" *Proc. Natl. Acad. Sci. USA* 95:7699–7704 (1998).

Valentine et al., "Self–Administration in Rats Allowed Unlimited Access to Nicotine" *Psychopharmacology*, 133:300–305 (1997).

Eliot L. Gardner, "6 Brain Reward Mechanisms", *Substance Abuse: A Comprehensive Textbook*, pp. 51–85 (1997).

Marshall et al., "Presynaptic Nicotinic Modulation of Dopamine Release in the Three Ascending Pathways Studied by In Vivo Microdialysis: Comparison of Naive and Chronic Nicotine–Treated Rats" *Journal of Neurochemistry*, 68:1511–1519 (1997).

M.–F. Chesselet, "Presynaptic Regulation of Neurotransmitter Release in the Brain", *Neuroscience* 12:347–375 (1984).

Lacey et al., "On the Potassium Conductance Increase Activated by $GABA_B$ and Dopamine $D_2$ Receptors in Rat Substantia Nigra Neurones" *Journal of Physiology* 401:437–453 (1988).

Grant et al., "Vigabatrin: A Review of its Pharmacodynamic an Pharmacokinetic Properties, and Therapeutic Potential in Epilepsy and Disorders of Motor Control" *Drugs* 41 6:889–926 (1991).

Jung et al., "Vinyl GABA (4–amino–hex–5–enoic acid). A New Selective Irreversible Inhibitor of GABA–T: Effects on Brain GABA Metabolism in Mice" *Neurochem.* 29:797–802 (1977).

Tsuji et al., "Activation of Ventral Tegmental $GABA_B$ Receptors Inhibits Morphine–Induced Place Preference in Rats" *European Journal of Pharmacology* 313:169–173.

Roberts et al., "Baclofen Suppression of Cocaine Self–Administration: Demonstration Using a Discrete Trials Procedure" *Psychopharmacology* 131:271–277 (1997).

Bolser et al., "The Pharmacology of SCH 50911: A Novel, Orally–Active GABA–B Receptor Antagonist" *The Journal of Pharmacology and Experimental Therapeutics* 274:1393–1398 (1995).

Roberts et al., "Baclofen Attenuates the Reinforcing Effects of Cocaine in Rats" *Neuropsychopharmacology* 15:417–423 (1996).

Derek van der Kooy, "Place Conditioning: A Simple and Effective Method for Assessing the Motivational Properties of Drugs" M.A. Bozarth, Ed., Springer–Verlag, New York, pp. 229–241 (1987).

Hurt et al., "A Comparison of Sustained–Release Bupropion and Placebo for Smoking Cessation" *The New England Journal of Medicine* 337:1195–1202 (1997).

Volkow et al., "Imaging Endogenous Dopamine Competition With [$^{11}$C] Raclopride in the Human Brain" *Synapse* 16:255–262 (1994).

Logan et al., "Graphical Analysis of Reversible Radioligand Binding from Time–Activity Measurements Applied to [N–$^{11}$C–methyl]–(–)–Cocaine PET Studies in Human Subjects" *Journal of Cerebral Blood Flow and Metabolism* 10:740–747 (1990).

Dewey et al., "A Novel Strategy for the Treatment of Cocaine Addiction" *Synapse* 30:119–129 (1998).

Dewey et al., "Striatal Binding of the PET Ligand $^{11}$C–Raclopride is Altered by Drugs that Modify Synaptic Dopamine Levels" *Synapse* 13:350–356 (1993).

Dewey et al. "GABAergic Inhibition of endogenous Dopamine Release Measured in vivo with $^{11}$C–Raclopride and Positron Emission Tomography" *The Journal of Neuroscience* 12(10):3773–3780 (1992).

Dewey et al., "Effects of Central Cholinergic Blockade on Striatal Dopamine Release Measured with Positron Emission Tomography in Normal Human Subjects" *Proc. Natl. Acad. Sci. USA* 90:11816–11820 (1993).

Buckland et al., "Amphetamine and Vigabatrin Down Regulate Aromatic L–amino acid Decarboxylase mRNA levels" *Molecular Brain Research* 35:69–76 (1996).

Cubells et al., "In Vivo Action of Enzyme–Activated Irreversible Inhibitors of Glutamic Acid Decarboxylase and γ–Aminobutyric Acid Transaminase in Retina vs. Brain" *The Journal of Pharmacology and Experimental Therapeutics* 238:508–514 (1986).

Herbert D. Kleber, "Treatment of Cocaine Abuse: Pharmacotherapy" *Cocaine Scientific and Social Dimensions* pp. 195–206 (1992).

Ritz et al., "Psychostimulant Drugs and a Dopamine Hypothesis Regarding Addiction: Update on recent research" *Biochem. Soc. Symp.* 59:51–64.

Sherif et al., "Basic Aspects of GABA–transmission in Alcoholism, with Particular Reference to GABA–transaminase" *European Neuropsychopharmacology* 7:1–7(1997).

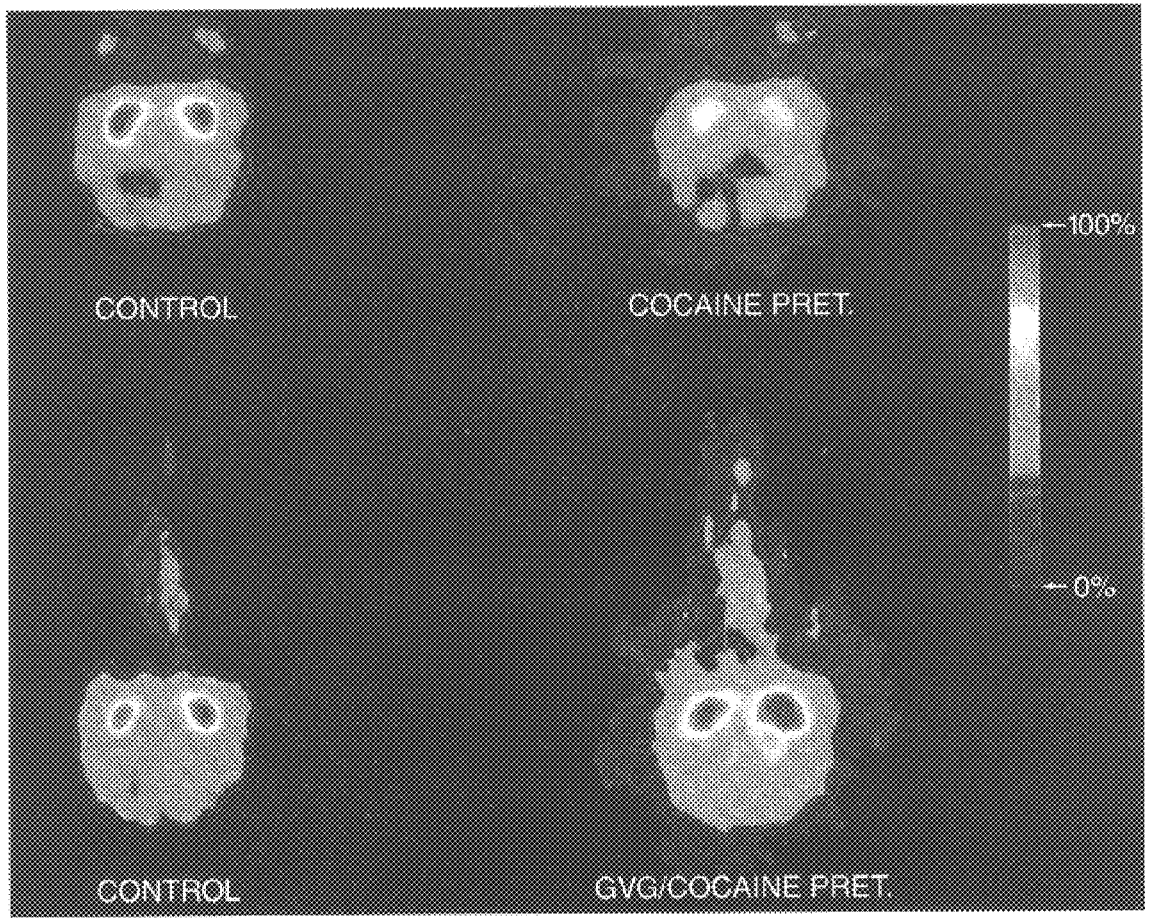

Transaxial parametric DV ratio images of the non-human primate brain as the level of the corpus striatum. The color scale indicates intensity of receptor availability (red indicates higher availability vs. magenta indicating a lower receptor availability). Cocaine decreases receptor availability (top right) compared to baseline values (top left). When pretreated with GVG, however, cocaine did not alter receptor availability (lower right) compared to baseline values (lower left).

FIGURE 2

Effects of GVG (150 mg/kg) on locomotor behavior compared with saline controls (open circles are GVG pretreated animals, closed circles are saline controls).

Effects of GVG (300 mg/kg) on locomotor behavior compared with saline controls (open circles are GVG pretreated animals, closed circles are saline controls).

TREATMENT OF ADDICTION AND ADDICTION-RELATED BEHAVIOR

This invention was made with Government support under Contract NO. DE-ACO2-98CH10886, between the U.S. Department of Energy and Brookhaven Science Associates and also under Contract Nos. NIMH MH49165, NIMH R2955155 between National Institutes of Mental Health and Brookhaven Science Associates. The Government has certain rights in the invention.

BACKGROUND OF THE INVENTION

This invention relates to the use of an irreversible inhibitor of GABA-transaminase for the treatment of substance addiction and modification of behavior associated with substance addiction. Substance addiction, such as drug abuse, and the resulting addiction—related behavior are enormous social and economic problems that continue to grow with devastating consequences.

Substance addiction can occur by use of legal and illegal substances. Nicotine, cocaine, and other addictive substances are readily available and routinely used by large segments of the United States population.

Many drugs of abuse are naturally occurring. For example, cocaine is a naturally occurring stimulant derived from the leaves of the coca plant, *Erythroylon coca*. Coca leaves contain only about one-half of one percent pure cocaine alkaloid, When chewed, only relatively modest amounts of cocaine are liberated, and gastrointestinal absorption is slow. Certainly, this explains why the practice of chewing coca leaves has never been a public health problem in Latin America. The situation changes sharply with the abuse of the alkaloid itself.

It has been found that addicting drugs have in common the enhancement (in some cases directly, in other cases indirectly or even trans-synaptically) of dopamine (DA) within the mesotelencephalic reward/reinforcement circuitry of the forebrain, presumably producing the enhanced brain reward that constitutes the drug user's "high". Alterations in the function of these DA systems have also been implicated in drug craving and in relapse to the drug-taking habit in recovering addicts. Cocaine acts on these systems by binding to the dopamine transporter (DAT) and preventing DA reuptake into the presynaptic terminal.

There is considerable evidence that cocaine's addictive liability is linked to reuptake blockade in central nervous system (CNS) reward/reinforcement pathways. For example, cocaine-induced increases in extracellular DA have been linked to its rewarding and craving effects in rodents. In humans, the pharmacokinetics binding profile of $^{11}C$-cocaine indicates that the uptake of labeled cocaine is directly correlated with the self-reported "high". In addition, human cocaine addicts exposed to cocaine-associated environmental cues experienced increased cocaine craving which is antagonized by the DA receptor antagonist haloperidol. Based upon the presumptive link between cocaine's addictive liability and the DA reward/reinforcement circuitry of the forebrain, many pharmacologic strategies for treating cocaine addiction have been proposed.

In the past, one treatment strategy was to target directly the DAT with a high-affinity cocaine analog, thereby blocking cocaine's binding. Another treatment strategy was to modulate synaptic DA directly by the use of DA agonists or antagonists. Yet another treatment strategy was to modulate synaptic DA, indirectly or trans-synaptically, by specifically targeting a functionally-linked but biochemically different neurotransmitter system.

A number of drugs have been suggested for use in weaning cocaine users from their dependency. Certain therapeutic agents were favored by the "dopamine depletion hypothesis." It is well established that cocaine blocks dopamine reuptake, acutely increasing synaptic dopamine concentrations. However, in the presence of cocaine, synaptic dopamine is metabolized as 3-methoxytyramine and excreted. The synaptic loss of dopamine places demands on the body for increased dopamine synthesis, as evidenced by the increase in tyrosine hydroxylase activity after cocaine administration. When the precursor supplies are exhausted, a dopamine deficiency develops. This hypothesis led to the testing of bromocriptine, a dopamine receptor agonist. Another approach was the administration of amantadine, a dopamine releaser. Yet another approach, also based on the dopamine depletion hypothesis, was to provide a precursor for dopamine, such as L-dopa.

Agonists are not preferred therapeutic agents. A given agonist may act on several receptors, or similar receptors on different cells, not just on the particular receptor or cell one desires to stimulate. As tolerance to a drug develops (through changes in the number of receptors and their affinity for the drug), tolerance to the agonist may likewise develop. A particular problem with the agonist bromocryptine, for example, is that it may itself create a drug dependency. Thus, treatment strategies used in the past did not relieve the patient's craving for cocaine. Moreover, by using certain agonists such as bromocryptine, a patient was likely to replace one craving for another.

Accordingly, there is still a need in the treatment of addiction to drugs of abuse to provide new methods which can relieve a patient's craving by changing the pharmacological actions of drugs of abuse in the central nervous system.

SUMMARY OF THE PRESENT INVENTION

The present invention, which addresses the needs of the prior art, provides methods for treating substance addiction and changing addiction-related behavior of a primate suffering from substance addiction by administering to the primate an effective amount of a pharmaceutical composition including gamma vinylGABA (GVG). The amount of GVG varies from about 100 mg to about 300 mg/kg, and preferably from about 150 mg/kg to about 300 mg/kg.

In a preferred embodiment, the present invention provides a method of eliminating the effects of nicotine addiction by treating a patient with an effective amount of a composition including GVG. When treating the effects of nicotine addiction the amount of GVG present in the pharmaceutical composition is preferably from about 75 mg/kg to about 150 mg/kg.

As a result of the present invention, methods of reducing substance addiction and changing addiction-related behavior are provided which are based on a pharmaceutical composition which is not itself addictive, yet is highly effective in ameliorating the addiction and the addictive behavior of addicted patients. The pharmaceutical composition useful for the method of the present invention inhibits or eliminates craving experienced by drug addicts. Moreover, the elimination of behavior associated with drugs of abuse occurs in the absence of an aversive or appetitive response to GVG. Moreover, behavior characteristics associated with dependency on drugs of abuse are reduced or eliminated in the absence of an alteration in the locomotor function of the primate.

Other improvements which the present invention provides over the prior art will be identified as a result of the following description which sets forth the preferred embodiments of the present invention. The description is not in any way intended to limit the scope of the present invention, but rather only to provide a working example of the present preferred embodiments. The scope of the present invention will be pointed out in the appended claims.

BRIEF DESCRIPTIONS OF THE DRAWINGS

FIG. 2 is a photograph of transaxial parametric DV ratio images of the non-human primate brain at the level of the corpus striatum.

DETAILED DESCRIPTION OF THE INVENTION

Figure 1:
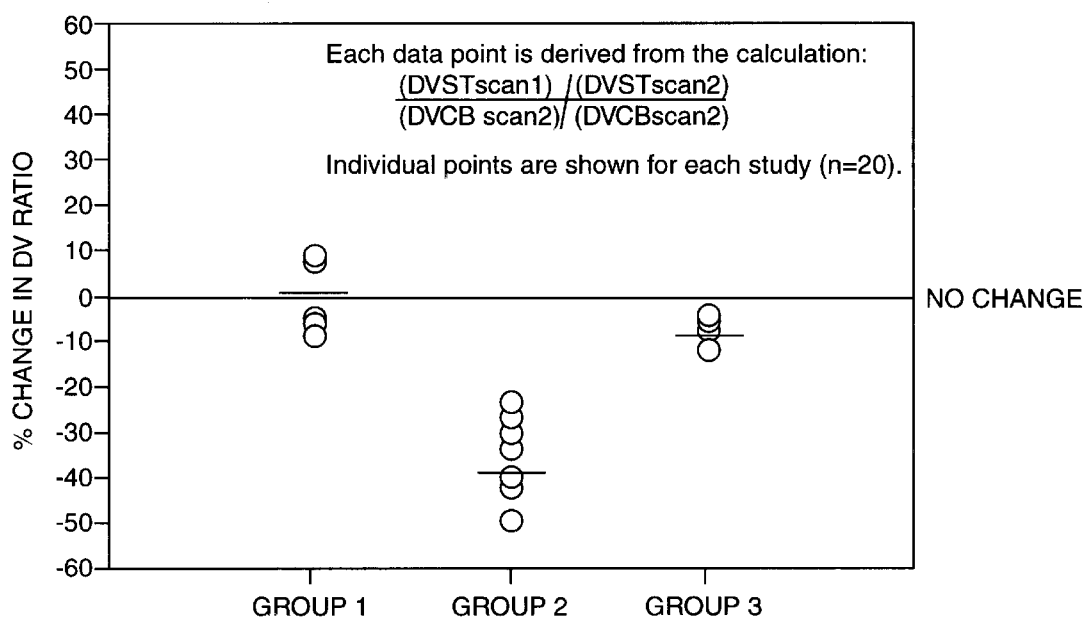
FIG. 1 is a graph illustrating percent change in distribution volume (DV) for three groups of animals treated with cocaine.

The present invention provides a highly efficient method for treating substance addiction and for changing addiction-related behavior of primates suffering from substance addiction.

As used herein, addiction-related behavior means behavior resulting from compulsive substance use and is characterized by apparent total dependency on the substance. Symptomatic of the behavior is (i) overwhelming involvement with the use of the drug, (ii) the securing of its supply, and (iii) a high probability of relapse after withdrawal.

For example, a cocaine user experiences three stages of drug effects. The first, acute intoxication ("binge"), is euphoric, marked by decreased anxiety, enhanced self-confidence and sexual appetite, and may be marred by sexual indiscretions, irresponsible spending, and accidents attributable to reckless behavior. The second stage, the ("crash"), replaces euphoria by anxiety, fatigue, irritability and depression. Some users have committed suicide during this period. Finally, the third stage, "anhedonia," is a time of limited ability to derive pleasure from normal activities and of craving for the euphoric effects of cocaine. See Gawin and Kleber, Medical Management of Cocaine Withdrawal, 6–8 (APT Foundation). As related to cocaine users, addiction-related behavior includes behavior associated with all three stages of drug effects.

Drugs of abuse include but are not limited to those acting as control stimulants such as cocaine, amphetamine, pipradol, methylphenidate, nicotine and caffeine. Drugs of abuse also include narcotics such as morphine and methadone, as well as CNS depressants such as barbiturates, chlordiazepoxide and ethanol.

Compulsive drug use includes three independent components: tolerance, psychological dependence and physical dependence. Tolerance produces a need to increase the dose of the drug after several administration in order to achieve the same magnitude of effect. Physical dependence is an adaptive state produced by repeated drug administration and which manifests itself by intense physical disturbance when drug administration is halted. Psychological dependence is a condition characterized by an intense drive or craving for a drug whose effects the user feels are necessary for a sense of well being. See Feldman, R. S. and Quenzer, L. F. "Fundamentals of Neuropsychopharmocology" 418–422 (Sinaur Associates, Inc.) 1984 incorporated herein by reference as if set forth in full. Based on the foregoing definitions, as used herein "dependency characteristics" include all characteristics associated with compulsive drug use, characteristics that can be affected by biochemical composition of the host, physical and psychological properties of the host.

As explained above, the compulsive use of drugs of abuse gives rise to a euphoric stage followed by a stage of craving for the euphoric effects of that drug. As used herein the rewarding/incentive effects of drugs of abuse refers to any stimulus (in this case, a drug) that produces hedonia or increases the probability of a learned response. This is synonymous with reinforcement. With respect to experimental animals a stimulus is deemed to be rewarding by using paradigms that are believed to measure reward. This can be accomplished by measuring whether stimuli produce an approach response, also known as an appetitive response or a withdrawal response, as when the animal avoids the stimuli, also known as an aversive response. Conditioned place preference (CPP) is a paradigm which measures approach (appetitive) or withdrawal (aversive) responses. One can infer that rewarding stimuli produce approach behavior. In fact, one definition of reward is any stimulus that elicits approach behavior. Furthermore, the consequences of reward would be to enhance the incentive properties of stimuli associated with the reward.

Reward can also be measured by determining whether the delivery of a reward is contingent upon a particular response, thereby increasing the probability that the response will reappear in a similar situation, i.e. reinforcement paradigm. For example, a rat pressing a bar a certain number of times for an injection of cocaine is an example of reinforcement. Yet another way to measure reward is by determining if a stimulus (e.g. a drug), through multiple pairings with neutral environmental stimuli, can cause the previously neutral environmental stimuli to elicit behavioral effects initially only associated with the drug—this conditioned reinforcement. CPP is considered to be a form of conditioned reinforcement.

The incentive motivational value of a drug (or other stimuli) can be assessed using conditioned place preference (CPP). With respect to cocaine, animals are tested in a drug-free state, to determine whether they prefer an environment in which they previously received cocaine as compared to an environment in which they previously received saline. In the CPP paradigm, animals are given a drug in one distinct environment and are given the appropriate vehicle in an alternative environment. The CPP paradigm is widely used to evaluate the incentive motivational effects of drugs in laboratory animals (Van Der Kooy, 1995). Following conditioning or pairing with the drug if the animal, in a drug-free state, consistently chooses the environment previously associated with cocaine, the inference is drawn that the appetitive value of cocaine was encoded in the brain and is accessible in the drug-free state. CPP is reflected in an increased duration spent in the presence of the drug-associated stimuli relative to vehicle-injected control animals.

It has been postulated that since craving at the human level is often elicited by sensory stimuli previously associated with drug-taking, conditioning paradigms like CPP may be used to model craving in laboratory animals.

The addictive liability of drugs of abuse, such as for example, cocaine, has been linked to their pharmacological actions on mesotelencephalic dopamine (DA) reinforcement/reward pathways in the central nervous system (CNS). Dopaminergic transmission within these pathways is modulated by gamma-amino butyric acid (GABA).

Cocaine inhibits the presynaptic reuptake of monoamines. Dopaminergic neurons of the mesocorticolimbic DA system, whose cell bodies lie within the ventral tegmental area (VTA) and project primarily to the nucleus accumbens (NACC), appear to be involved in cocaine reinforcement. Electrical stimulation of reward centers within the VTA increases extracellular DA levels in the NACC, while 6-hydroxy dopamine lesions of the NACC abolish cocaine self-administration. In vivo microdialysis studies confirm cocaine's ability to increase extracellular DA in the NACC.

γ-Amino butyric acid (GABA)ergic neurons in the NACC and ventral pallidum project onto DA neurons in the VTA. Pharmacologic and electrophysiologic studies indicate these projections are inhibitory. Inhibition of VTA-DA neurons is likely the result of $GABA_B$ receptor stimulation. In addition, microinjection of baclofen into the VTA, acting via these receptor subtypes, can decrease DA concentrations in the NACC. Taken together, it is evident that pharmacologic manipulation of GABA may effect DA levels in the NACC through modulation of VTA-DA neurons.

Gamma vinyl GABA (GVG) is a selective and irreversible inhibitor of GABA-transaminase (GABA-T) known to potentiate GABAergic inhibition. It is also known that GVG alters cocaine's biochemical effects by causing a dose-dependent and prolonged elevation of extracellular endogenous brain GABA levels.

GVG is $C_6H_{11}NO_2$ or 4-amino-5-hexanoic acid available as Vigabatrin® from Hoechst Marion Roussel and can be obtained from Marion Merell Dow of Cincinnati, Ohio. GVG does not bind to any receptor or reuptake complex, but increases endogenous intracellular GABA levels by selectively and irreversibly inhibiting GABA-transaminase (GABA-T), the enzyme that normally catabolizes GABA.

Based on the knowledge that cocaine increases extracellular NACC DA and the fact that GABA inhibits DA in the same nuclei, one of us has shown that GVG can attenuate cocaine-induced changes in extracellular DA. Specifically, in vivo microdialysis techniques were used in freely moving animals to show, the effects of acute (single injection) and chronic (11 days) GVG administration on cocaine-induced increases in extracellular DA concentration in the NACC. See specifically Morgan, A. E., et al. "Effects of Pharmacologic Increases in Brain ABA Levels on Cocaine—Induced Changes in Extracellular Dopamine,"Synapse 28:60–65 (1998) the contents of which are incorporated herein as if set forth in full.

It has unexpectedly been found that intake of GVG alters behavior, and especially addiction-related behavior associated with the biochemical changes resulting from intake of drugs of abuse. For example, GVG significantly attenuated cocaine-induced increases in neostriatal synaptic DA in the primate (baboon) brain as assessed by positron emission tomography (PET) and abolished both the expression and acquisition of cocaine-induced conditioned place preference or CPP. It had no effect, however, on CPP for a food reward or on the delivery of cocaine to the brain locomotor activity. These findings suggest the possible therapeutic utility in cocaine addiction of a pharmacologic strategy targeted at the GABAergic neurotransmitter system, a system distinct from but functionally linked to the DA mesotelencephalic reward/reinforcement system. However, rather than targeting the GABA receptor complex with a direct GABA agonist, this novel approach with GVG takes advantage of the prolonged effects of an irreversible enzyme inhibitor that raises endogenous GABA levels without the addictive liability associated with GABA agonists acting directly at the receptor itself.

Details of the invention have been set forth herein in the form of examples which are described below. The full scope of the invention will be pointed out in the appended claims.

EXAMPLES

Examples have been set forth below for the purpose of illustration and to describe the best mode of the present invention. The scope of the invention is not to be in any way limited by the examples set forth herein.

MATERIALS AND METHODS

1. Primate PET Studies

Twenty adult female baboons (Papio anubis, 13–18 kg) were used for all studies and carbon-11 labeled raclopride, previously shown to be sensitive to changes in synaptic DA was synthesized as previously described (Volkow, et al., 1994). Arterial blood samples were obtained throughout the study and selected plasma samples were analyzed for the presence of unchanged radio tracer carbon-11. Animals were not removed from the gantry between isotope injections. Regions of interest (ROI's) were drawn directly on the PET images. Briefly, the corpus striatum was outlined, bilaterally, on every transaxial slice upon which it appeared. The cerebellar ROI was drawn across the midline at the level of the cerebellar vermis. ROI's from the first study were then copied directly onto the corresponding slice from the second. By examining placement of the ROI's on the second scan changes could be made, if necessary, in ROI position only. This multi planar method of analysis reduced differences that may arise due to movement of the animal within the gantry during the scanning interval.

A graphical method for determining the distribution volume (DV) was developed previously for the kinetic analysis of the $[^{11}C]$-raclopride data. The DV ratio was the most reproducible measure of raclopride uptake. The ratio is the DV from a receptor-rich region (corpus striatum) to the DV of a non-receptor region (cerebellum). The free receptor concentration was directly proportional to the DV ratio of 1. Animal preparation was conducted as detailed previously (Dewey, et al., 1992).

The statistical analysis was designed to test the hypothesis that (1) the cocaine challenge differed from the test/retest variability of the radio tracer carbon-11 (performed in the same animals under identical experimental conditions) and (2) the challenge conditions differed from each other. The fact that significant results were obtained for the striatum and striatum to cerebellum ratio, but not for the cerebellum, indicated that the effects of the intervention were limited to the specific, but not the non-specific binding component. GVG did not alter the regional distribution nor the rate of metabolism of the radio tracer.

2. Cocaine-Induced Conditioned Place Preference in Rodents

In all rodent studies, male Sprague-Dawley rats were used (200–225 g, Taconic farms, Germantown, N.Y.). Animals were allowed to acclimate to the animal housing facility for at least 5 days prior to beginning the experiments. We used conditioned place preference (CPP) chambers as previously described (Lepore et al., 1995), except instead of one chamber being entirely white and the other black, one chamber was entirely light blue with a stainless steel floor and the second chamber was light blue with horizontal black stripes (2.5 cm wide) spaced 3.8 cm apart with a smooth plexiglass floor. In all CPP studies with GVG, the saline volume was (1 ml/kg), and the cocaine doses were 20 mg/kg. The saline, cocaine and GVG were all injected intraperitonealy (i.p.). The conditioning procedure for the acquisition phase consisted of 12 sessions carried out consecutively over 12 days.

The CPP pairings were: 1) saline/saline 2) saline/cocaine 3) GVG/saline 4) saline/cocaine and GVG. The animals in each group were randomly assigned to a 2×2 factorial design with one factor being the pairing chamber and the other factor being the order of conditioning. The animals that received either saline or cocaine were injected and confined to the appropriate compartment for 30 minutes. The GVG injections were given 3 hours before saline or cocaine injection and subsequent placement of the animals in the appropriate chamber. This was done as it has been shown that GABA levels reach maximal values 3 to 4 hours following GVG administration.

On the test day (day 12), neither drugs nor saline were administered and the animal was allowed to move freely between both chambers for fifteen minutes. The amount of time spent in each chamber was recorded using an automated infrared beam electronically coupled to a timer. For the expression phase of CPP to cocaine, the animals were habituated and conditioned to cocaine as described in the acquisition studies, but no animals in the expression studies were given GVG on conditioning days. On the test day (day 12), the animals being tested in the expression phase, unlike the animals in the acquisition phase, received either saline or GVG 2.5 hours before they were placed in the apparatus and allowed free access to both chambers for 15 minutes.

3. Food-Induced Conditioned Place Preference in Rodents

In order to test food-induced CPP in rodents, four groups of rats were allowed access to food ad libitum during the entire 12 session of CPP procedure. The 12 session CPP procedure was exactly the same as the procedure used in the cocaine induced CPP studies except the appetitive substance was food rather than cocaine. Group one was given saline, group two was given intraperitonially 150 mg/kg of GVG, group 3 was given saline and group 4 was given intraperitonially 300 mg/kg of GVG prior to food exposure and CPP pairing to a side of the CPP box. The animals in all four groups were habituated to Froot Loops, a fruit-flavored breakfast cereal that is very appealing to laboratory rats, in the appropriate chamber in the test room during four habituating sessions. Twenty-four hours after the last CPP pairing, the animals were placed in the chamber and neither drug nor saline (nor food) was administered (nor available) and animals were allowed to move freely within the CPP apparatus for 15 minutes. The amount of time spent in the paired and unpaired chambers was recorded using an automated device.

4. Locomotor Activity Measured in Rodents

Animals were prehandled for 5 minutes each day for one week prior to the experiment to reduce handling stress. On the day of the study, GVG (150 mg/kg or 300 mg/kg) or saline (1 ml/kg or 0.5 ml/kg) was administered intraperitonially 2.5 hours prior to the experiment. The animals were transported to the testing area one hour before each experiment. 2.5 hours after GVG or saline administration, animals were placed in the behavior cages and the locomotor activity was recorded in 10 minute intervals for 90 minutes onto a PC-AT computer using the hardware for the Photobeam Activity System. The locomotor cages themselves are 41.3×41.3×30.5 cm clear acrylic cages. The electronic system (Photobeam Activity system, San Diego Instruments, San Diego, Calif.) used to monitor locomotor activity consists of 16 infrared beams projecting across the cages from left to right and 16 beams from front to back. All the infrared beams are approximately 0.39 cm from the floor.

5. Catalepsy Studies in Rodents

The degree of catalepsy following the administration intraperitonially of 150 mg/kg GVG, 300 mg/kg intraperitonially GVG or saline (1 ml/kg, i.p. 0.9% saline) was determined by using the Bar test (Ferre, et al., 1996). Briefly, male Sprague-Dawley rats were handled and transported to the test room three days prior to the experiments to allow for acclimation. On the test day, the animals (n=10 per treatment group) received either saline or GVG, and the degree of catalepsy was measured 60, 120 and 240 minutes following injection. The experimenter was blind to the treatment received by each animal. The bar was composed of wood and had a diameter of 1.2cm and height from floor to the top of the bar was 10 cm. For each determination, the forepaws of the animals were gently placed over the bar and the time it took the animal to move both forepaws to the floor was measured.

6. [$^{11}$C]-Cocaine Studies in Rodents and Primates

Animals (n=10) were placed into two groups. In group 1, saline (1 ml/kg) was administered via intraperitoneal (i.p.) injection 3 hours prior to i.p. [$^{11}$C]-cocaine administration. In group 2, GVG (300 mg/kg) was administered via i.p. injection 3 hours prior to i.p. [$^{11}$C]-cocaine administration. Animals were sacrificed 10 minutes following [$^{11}$C]-cocaine injection. Brains were removed and counted for radioactivity. In two additional primate PET studies, GVG was administered (300 mg/kg) immediately following a baseline scan with labeled cocaine. Approximately 3 hours later, labeled cocaine was again administered and animals were scanned for 60 minutes.

7. Microdialysis studies in Rodents

All animals were used under an IACUC-approved protocol and with strict adherence to the NIH guidelines. Adult male Sprague-Dawley rats (200–300 g, Taconic Farms), housed in the animals care facility under 12:12 light/dark conditions, were placed into 6 groups (n=5–9), anesthetized and siliconized guide cannulae were stereotactically implanted into the right NACC (2.0 mm anterior and 1.0 mm lateral to bregms, and 7.0 mm ventral to the cortical surface) at least 4 days prior to study. Microdialysis probes (2.0 mm, Bioanalytical Systems, BAS, West Lafayette, Ind.) were positioned within the guide cannulae and artificial cerebrospinal fluid (ACSF, 155.0 mM NA$^-$, 1.1 mM Ca$^{2-}$, 2.9 mM K; 132.76 mM Cl$^-$, and 0.83 mM Mg$^{2-}$) was administered through the probe using a CMA/100 microinfusion pump (BAS) at a flow rate of 2.0 $\mu$l/min. Animals were placed in bowls, and probes were inserted and flushed with ACSF overnight. On the day of the study, a minimum of three samples were injected to determine baseline stability. Samples were collected for 20 min. and injected on-line (CMA/160, BAS). The average Dopamine concentration of these three stable samples was defined as control (100%), and all subsequent treatment values were transformed to a percentage of that control. Upon establishing a stable baseline, the nicotine was administered by intraperitoneal (ip) injection. The high performance liquid chromatography (HPLC) system consists of a BAS reverse-phase column (3.0µC-18), a BAS LC-4C electrochemical transducer with a dual/glassy carbon electrode set at 650 mV, a computer that analyzes data on-line using a commercial software package (Chromograph Bioanalytical Systems), and a dual pen chart recorder. The mobile phase (flow rate 1.0 ml/min) consisted of 7.0% methanol, 50 mM sodium phosphate monobasic, 1.0 mM sodium octyl sulfate, and 0.1 mm EDNA, pH 4.0. DA eluted at 7.5 min. Upon completion of the study, animals were decapitated and frozen sections were obtained for probe placement verification.

In parallel to the quantitative estimates of dopamine concentration, the locomotor response of these animals to stimulant administration was simultaneously quantified using an infrared motion sensor. This infrared optical proximity detector monitored movement of the gimbaled arm, an integral component of the freely moving system. The digital output of the detector was interfaced with an IBM personal computer and programmed to count both positive and negative arm deflections. These data were collected and totaled using the same temporal sampling protocol used for the dialysis samples. Locomotor activity was then expressed as the number of deflections per sample interval.

EXAMPLE 1

Non-Human Primate (Baboon) Studies

In this example twenty non-human primates received two [$^{11}$C]-raclopride injections in accordance with the procedure described in Section 1 of Materials and Methods. The first served as a baseline and the second followed cocaine or placebo. Test/retest primates (n=7) shown as Group 1 of Table 1 below received placebo (0.9% saline, 1 ml/kg) prior to the second radio tracer injection in order to determine the test/retest variability of this imaging method.

TABLE I

Groups and experimental conditions

| Group | Pharmacologic condition |
|---|---|
| 1 | Control (test/retest) |
| 2 | Cocaine treated |
| 3 | GVG/Cocaine treated |

All remaining primates (n=13) received a systemic injection of cocaine hydrocloride (0.5, 1.0 or 2.0 mg/kg) either 5 or 30 minutes prior to the second [$^1$C]-raclopride injection. Of these 13 animals, five received GVG (300 mg/kg, iv) 3 hours prior to cocaine administration.

Different cocaine doses and cocaine pretreatment time intervals produced no significant changes in the effects of cocaine on the distribution volume (DV), in line with expectations. Thus, the average % change in the DV ratio for animals treated with cocaine alone (n=8) versus GVG/cocaine (n=5) as Groups 2 and 3 of FIG. 1 respectively.

As a competitive antagonist, [$^{11}$C]-raclopride's binding is dependent upon the concentration of DA in the synaptic cleft. That is, as synaptic DA concentrations decrease, [$^{11}$C]-raclopride binding increases. Conversely, as synaptic DA concentrations increase, [$^{11}$C]-raclopride binding decreases. As seen in FIG. 1, the test/retest variability of this imaging method was less than 7% for group 1. The variability of these PET measurements is consistent with previous values obtained with [$^{11}$C]-raclopride in primates. In Group 2, cocaine produced a greater than 30% reduction in the mean DV ratio (p<0.0002, Student's two-tailed t-test, FIG. 1). These data are consistent with simultaneous PET and microdialysis studies in which an amphetamine challenge increased extracellular DA and decreased [$^{11}$C]-raclopride binding in the primate brain. In addition, these findings are similar to a recent report which examined the effects of a cocaine challenge on labeled raclopride binding in the human. Finally, these data are consistent with our own microdialysis studies (Morgan and Dewey, 1998) as well as our primate and human PET studies with amphetamine, GBR 12909, tetrabenazine, methylphenidate, and [$^{11}$C]-raclopride (Dewey et al., 1993; Volkow, et al., 1994). GVG pretreatment, however, significantly blocked the cocaine-induced decrease as shown in Group 2 of FIG. 1 in the DV ratio (group 2, p<0.002, Student's two-tailed t-test). These differences are readily apparent in the parametric DV ratio images as shown in FIG. 2. Values for groups 1 and 3 were not statistically different (p>0.1, Student's two-tailed t-test).

EXAMPLE 2

Cocaine-Induced Conditioned Place Preference Studies in Rodents

In this example the procedure outlined in Section 2 of Materials and Methods was followed. Cocaine produced a dose-dependent CPP response, with the most reliable and robust response occurring at 20 mg/kg as shown in Table 2 below.

TABLE II

Conditioned place preference to cocaine

| | Time spent in chambers (mins) | |
|---|---|---|
| Cocaine (mg/kg) | Paired | Unpaired[1] |
| 0 | 7.4 ± 0.3 | 7.6 ± 0.3 |
| 5.0 | 8.2 ± 0.4 | 6.8 ± 0.5 |
| 10.0 | 9.6 ± 0.5[2] | 5.4 ± 0.3 |
| 20.0 | 11.8 ± 0.4[3] | 3.2 ± 0.4[4] |

[1]Monitored animals were injected only with saline
[2]Significantly greater than the 0 and 5 mg/kg doses of cocaine, p < 0.05, analysis of variance (ANOVA) and Student-Newman-Keuls test.
[3]Significantly greater than the 0.5 and 10 mg/kg doses of cocaine, p < 0.05, ANOVA and Student-Newman-Keuls test.
[4]Significantly less than 0.5 and 10 mg/kg doeses of cocaine, p < 0.01, ANOVA and Student-Newman-Keuls test.

We therefore chose a 20 mg/kg cocaine dose with which to examine the effect of GVG administration on the acquisition and expression phases of cocaine-induced CPP. The results clearly indicated that 112, 150 and 300 mg/kg, but not 75 mg/kg, of GVG blocked the acquisition and expression of cocaine-induced CPP. See specifically Tables 3–10 below.

TABLE III

Effect of GVG and saline on the acquisition of cocaine induced conditioned place preference

| Treatment pairings[1] | Time spent in chambers (min) | |
|---|---|---|
| | Paired | Unpaired[2] |
| Saline/Saline | 7.3 ± 0.5 | 7.7 ± 0.6 |
| Saline/Cocaine | 11.1 ± 0.3[4] | 3.9 ± 0.4 |
| 75 mg/kg GVG[3]/Saline | 7.3 ± 0.5 | 7.7 ± 0.6 |
| 75 mg/kg GVG[3]/Cocaine | 9.1 ± 1.1 | 5.9 ± 1.2 |

[1]Each value represents the mean number of minutes spent in each chamber ± S.E.M. (n = 8–10).
[2]Monitored animals were injected only with saline.
[3]Animals received GVG or Saline 2.5 hours prior to receiving saline or cocaine (20 mg/kg).
[4]Significantly greater than all treatment groups, p < 0.05, ANOVA and Newman-Keuls Test.
[5]Significantly less than all treatment groups, p < 0.01, ANOVA and Newman-Keuls test.

TABLE IV

| Treatment pairings[1] | Time spent in chambers (mins) | |
|---|---|---|
| | Paired | Unpaired[2] |
| Saline/Saline | 7.2 ± 0.5 | 7.8 ± 0.4 |
| Saline/Cocaine | 11.8 ± 0.5[4] | 3.2 ± 0.5 |
| 112 mg/kg GVG[3]/Saline | 7.6 ± 0.6 | 7.4 ± 0.6 |
| 112 mg/kg GVG[3]/Cocaine | 8.2 ± 0.5 | 6.8 ± 0.5 |

[1]Each value represents the mean number of minutes spent in each chamber ± S.E.M. (n = 8–10).
[2]Monitored animals were injected only with saline.
[3]Animals received GVG or Saline 2.5 hours prior to receiving saline or cocaine (20 mg/kg).
[4]Significantly greater than all treatment groups, p < 0.05, ANOVA and Newman-Keuls Test.
[5]Significantly less than all treatment groups, p < 0.01, ANOVA and Newman-Keuls test.

TABLE V

| Treatment pairings[1] | Time spent in chambers (mins) | |
|---|---|---|
| | Paired | Unpaired[2] |
| Saline/Saline | 7.4 ± 0.3 | 7.6 ± 0.4 |
| Saline/Cocaine | 11.6 ± 0.5[4] | 3.4 ± 0.4[5] |
| 150 mg/kg GVG[3]/Saline | 7.8 ± 0.6 | 7.2 ± 0.6 |
| 150 mg/kg GVG[3]/Cocaine | 7.9 ± 0.8 | 7.1 ± 0.8 |

[1]Each value represents the mean number of minutes spent in each chamber ± S.E.M. (n = 8–10).
[2]Monitored animals were injected only with saline.
[3]Animals received GVG or Saline 2.5 hours prior to receiving saline or cocaine (20 mg/kg).
[4]Significantly greater than all treatment groups, p < 0.05, ANOVA and Newman-Keuls Test.
[5]Significantly less than all treatment groups, p < 0.01, ANOVA and Newman-Keuls test.

TABLE VI

| Treatment pairings[1] | Time spent in chambers (mins) | |
|---|---|---|
| | Paired | Unpaired[2] |
| Saline/Saline | 7.7 ± 0.3 | 7.3 ± 0.3 |
| Saline/Cocaine | 11.2 ± 0.6[4] | 3.8 ± 0.5[5] |
| 300 mg/kg GVG[3]/Saline | 7.2 ± 0.4 | 7.8 ± 0.4 |
| 300 mg/kg GVG[3]/Cocaine | 7.6 ± 0.7 | 7.2 ± 0.7 |

[1]Each value represents the mean number of minutes spent in each chamber ± S.E.M. (n = 8–10).
[2]Monitored animals were injected only with saline.
[3]Animals received GVG or Saline 2.5 hours prior to receiving saline or cocaine (20 mg/kg).
[4]Significantly greater than all treatment groups, p < 0.05, ANOVA and Newman-Keuls Test.
[5]Significantly less than all treatment groups, p < 0.01, ANOVA and Newman-Keuls test.

TABLE VII

Effect of GVG and saline on the expression of cocaine-induced conditioned place preference

| Treatment pairings[1] | Drug given on test day | Time spent in chambers (min) | |
|---|---|---|---|
| | | Paired | Unpaired[2] |
| Saline/Saline | Saline | 7.5 ± 0.41 | 7.5 ± 0.4 |
| Saline/Sahne | GVG, 75 mg/kg | 7.5 ± 0.3 | 7.5 ± 0.3 |
| Saline/Cocaine | Saline | 11.8 ± 0.5[3] | 3.2 ± 0.5 |
| Saline/Cocaine | GVG, 75 mg/kg | 10.6 ± 0.6[3] | 4.4 ± 0.9 |
| Saline/Saline | Saline | 7.8 ± 0.5[1] | 7.2 ± 0.6 |

[1]Each value represents the mean number of minutes spent in each chamber ± S.E.M. (n = 10).
[2]Monitored animals were injected only with saline.
[3]Significantly greater than all other treatment paintings, p < 0.01, ANOVA and Student Newman-Keuls test.

TABLE VIII

| Treatment pairings[1] | Drug given on test day | Time spent in chambers (min) | |
|---|---|---|---|
| | | Paired | Unpaired[2] |
| Saline/Saline | Saline | 7.1 ± 0.5 | 7.9 ± 0.5 |
| Saline/Saline | GVG, 112 mg/kg | 7.2 ± 0.3 | 7.8 ± 0.3 |
| Saline/Cocaine | Saline | 12.2 ± 0.6[3] | 2.8 ± 0.5 |
| Saline/Cocaine | GVG, 112 mg/kg | 8.1 + 0.7 | 6.9 ± 0.6 |

[1]Each value represents the mean number of minutes spent in each chamber ± S.E.M. (n = 10).
[2]Monitored animals were injected only with saline.
[3]Significantly greater than all other treatment pairings, p < 0.01, ANOVA and Student Newman-Keuls test.

TABLE IX

| Treatment pairings[1] | Drug given on test day | Time spent in chambers (min) | |
|---|---|---|---|
| | | Paired | Unpaired[2] |
| Saline/Saline | Saline | 7.2 ± 0.2[1] | 7.8 ± 0.2 |
| Saline/Saline | GVG, 150 mg/kg | 7.7 ± 0.2 | 7.3 ± 1.1 |
| Saline/Cocaine | Saline | 11.1 ± 0.5[3] | [1,1]3.9 ± 0.4[4] |
| Saline/Cocaine | GVG, 150 mg/kg | 7.9 ± 0.3 | 7.1 ± 0.3 |

[1]Each value represents the mean number of minutes spent in each chamber ± S.E.M. (n = 10).
[2]Monitored animals were injected only with saline.
[3]Significantly greater than all other treatment pairings, p < 0.01, ANOVA and Student Newman-Keuls test.
[4]Significantly less than all other treatment pairings, p < 0.01, ANOVA and Student Newman-Keuls test.

TABLE X

| Treatment pairings[1] | Drug given on test day | Time spent in chambers (min) | |
|---|---|---|---|
| | | Paired | Unpaired[2] |
| Saline/Saline | Saline | 7.8 ± 0.5[1] | 7.2 ± 0.6 |
| Saline/Saline | GVG, 300 mg/kg | 7.3 ± 0.4 | 7.7 ± 0.3 |
| Saline/Cocaine | Saline | 12.5 ± 0.8[3] | 2.5 ± 0.6[4] |
| Saline/Cocaine | GVG, 300 mg/kg | 7.9 ± 0.5 | 7.1 ± 0.6 |

[1]Each value represents the mean number of minutes spent in each chamber ± S.E.M. (n = 10).
[2]Monitored animals were injected only with saline.
[3]Significantly greater than all other treatment pairings, p < 0.05, ANOVA and Student Newman-Keuls test.
[4]Significantly less than all other treatment pairings, p < 0.05, ANOVA and Student Newman-Keuls test.

EXAMPLE 3

Food-Induced Conditioned Place Preference Studies in Rodents

In this example the procedure outlined in Section 3 of Materials and Methods was followed. The results set forth in Table 11 below indicates that food elicited an incentive or rewarding effect. For example, all paired values show that rodents spent more time in the chamber where food was present.

TABLE XI

Effect of GVG (150, 300 mg/kg, ip) on conditioned place preference to food

| Treatment pairings | Time spent in chambers (min) | |
|---|---|---|
| | Paired | Unpaired[2] |
| Saline/Saline | 7.3 ± 0.6 | 7.7 ± 0.6 |
| GVG/Saline | 7.5 ± 0.7 | 7.5 ± 0.7 |
| Saline/Food | 9.3 ± 0.7 | 5.7 ± 0.7 |
| GVG (150 mg/kg)/Food | 9.4 ± 0.4 | 5.6 ± 0.5 |
| GVG (300 mg/kg)/Food | 9.0 ± 0.5 | 6.0 ± 0.5 |

[1]Each value represents the mean number of minutes spent in each chamber ± S.E.M.
[2]Monitored animals were injected only with saline.

The administration of 150 or 300 mg/kg of GVG did not alter the CPP response to food as shown in Table 11 despite attenuating the incentive motivational effects of cocaine in the above noted CPP experiments as shown in Tables 3–10 above.

Discussion of Experimental Results Obtained in Examples 1, 2 and 3

In previous PET studies, we showed that GVG alone reduces extracellular DA concentrations resulting in an increase in [$^{11}$C]-raclopride binding in the primate brain (Dewey, et al., 1992). In the PET studies of the present invention, GVG-induced decreases in extracellular DA levels prior to cocaine administration clearly underlie the attenuation of cocaine's effects observed in group 3 of Table 1. However, the seemingly identical values found for groups 1 and 3, combined with our previous findings using GVG alone (Dewey, et al., 1992), indicate that cocaine increased extracellular DA levels in the present invention despite GVG administration, but only to baseline values.

However, based on the CPP data presented here, this cocaine-induced return to baseline was apparently insufficient to produce incentive motivational effects. Our results indicate that cocaine produced a CPP response. In contrast, vehicle pairings did not produce a CPP response, indicating that the animals did not display a chamber preference, i.e., the apparatus is unbiased. In addition, the CPP response to cocaine was dose-dependent, with the most reliable and robust response occurring at the 20 mg/kg cocaine dose.

Administration of 112, 150, 300 mg/kg but not 75 mg/kg of GVG blocked the acquisition and expression of the CPP response elicited by cocaine. In contrast, GVG, when paired with saline, did not produce a CPP or aversive response. This indicates that the blockade of the CPP to cocaine by GVG was not related to GVG's eliciting an aversive or appetitive response by itself. Our results presented in Example 2 indicated that food elicits an incentive or rewarding effect. The administration of 150 or 300 mg/kg of GVG did not alter the CPP response to food, despite attenuating the incentive effects of cocaine. This finding suggests that GVG specifically attenuates the rewarding/incentive effects of cocaine.

EXAMPLE 4

Locomotor Activity and Catalepsy Studies in Laboratory Rodents

Figure 3A:
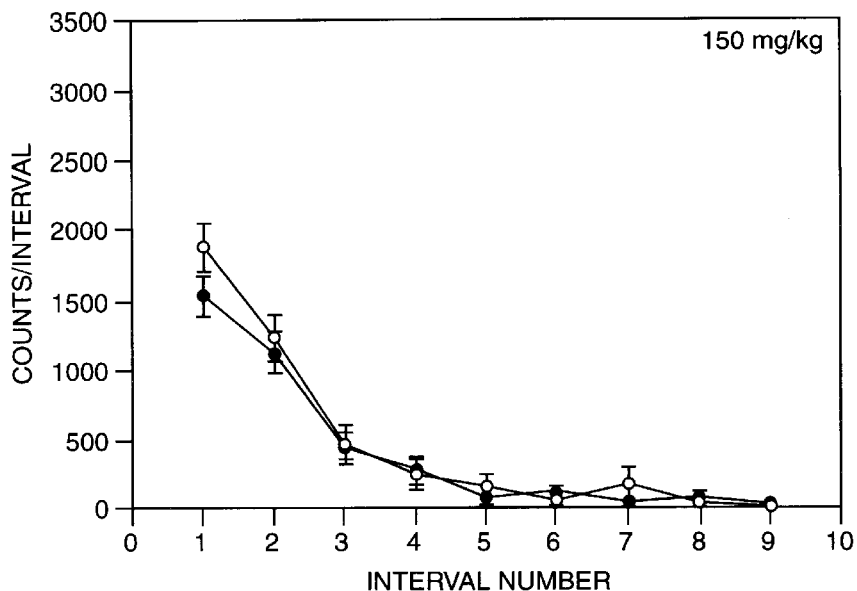
FIGS. 3A and 3B are graphs illustrating the effects of GVG on locomotor behavior as compared with saline controls.
Figure 3B:
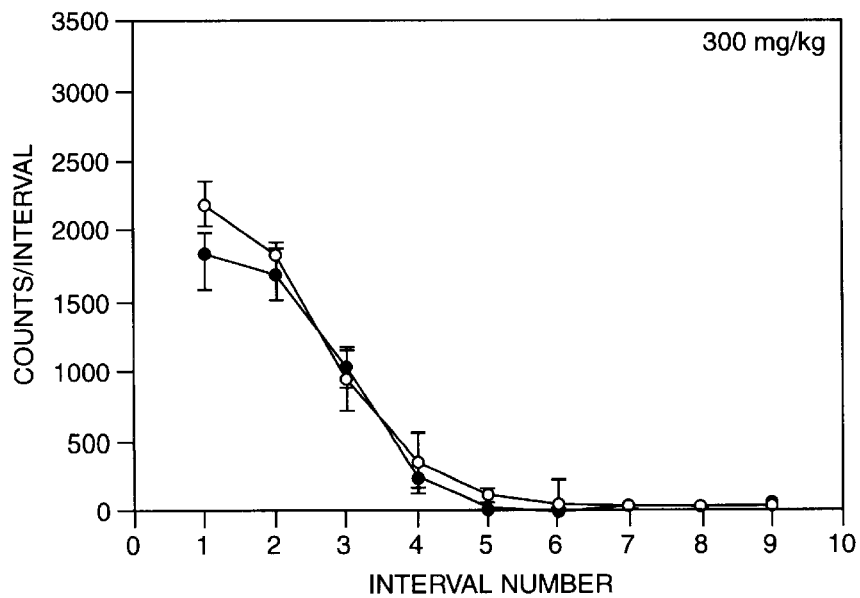

In this example the procedures outlined in Section 4 and 5 of Materials and Methods were followed. Although it is widely accepted that the CPP paradigm differentiates incentive motivational effects from motoric effects, we nevertheless assessed GVG's effects on locomotion and catalepsy in rats. We found that pretreatment with GVG at doses of 150 mg/kg or 300 mg/kg did not alter locomotor activity compared to saline pretreated controls as shown in FIGS. 3a and 3b. In addition, pretreatment with GVG at doses of 150 mg/kg or 300 mg/kg did not induce catalepsy in rats. Catalepsy duration after 300 mg/kg GVG was 1.1+0.4 seconds (n=10), which was not significantly different from 0.7+0.3 seconds (n=10) in saline-treated rats. n indicates the number of rodents which were tested.

EXAMPLE 5

$^{11}$C-Cocaine levels in Rodents and Primates

In this example the procedure outlined in Section 6 of Materials and Methods was followed. In order to assess the possibility that GVG could attenuate cocaine's actions by altering its penetration into the brain, we examined the effect of saline and GVG on [$^{11}$C]-cocaine levels in the whole rat and primate brain. In rodents, the levels of [$^{11}$C]-cocaine in the brain following intraperitoneal administration of saline and 300 mg/kg GVG were 0.110±0.03 and 0.091±0.02, respectively, which did not statistically differ. In primates, the pharmacokinetic profile of labeled cocaine binding in the neostriatum was not significantly different from the baseline scan both in terms of absolute uptake as well as clearance.

EXAMPLE 6

In this example, the effects of GVG on nicotine-induced changes in extracellular dopamine concentrations were measured in freely moving rats. The procedure outlined in Section 7 of Materials and Methods was followed.

A total of 8 rats were examined for each treatment pairing. Animals received 4 pairings over an 8 day period, one pairing per day.

Animals received 75 mg/kg of GVG 2.5 hours prior to receiving 0.4 mg/kg of nicotine. Animals were given GVG, then nicotine and placed in the appropriate chamber on day 1. On day 2, the animals were given GVG, then saline and placed in the appropriate chamber. The protocol on days 1 and 2 was repeated 3 additional times. Twenty four hours after the last pairing was administered, the animals were allowed free access to the entire behavioral apparatus for 15 minutes and the amount of time spent in the paired and unpaired chambers recorded using an automated device. The effects of 75 mg/kg of intraperitoneally applied GVG on acquisition of CPP to nicotine by the rats examined in this example is set forth in Table XII below.

TABLE XII

Effect of 75 mg/kg i.p. GVG on acquisition of conditioned place preference to (−)-nicotine.

| Treatment Pairings | Time spent in chambers (min)[1] | |
|---|---|---|
| | Paired | Unpaired[2] |
| Nicotine 0.4 mg/kg, s.c./Vehicle[3] | 9.4 ± 0.5 | 5.6 ± 0.5 |
| 75 ,g/kg GVG/Nicotine, 0.4 mg/kg, s.c. | 6.4 ± 0.3[4] | 8.6 ± 0.3[5] |

[1]Each value represents the mean number of minutes spent in each chamber ± S.E.M.
[2]Monitored animals were injected only with saline.
[3]The vehicle was 1 ml/kg of 0.9% NaCl or saline solution.
[4]Significantly less than nicotine/vehicle pairing, $p < 0.01$, ANOVA and Student-Newman-Keuls test.
[5]Significantly greater than nicotine/vehicle pairing, $p < 0.01$, ANOVA and Student-Newman-Keuls test.

Figure 4:
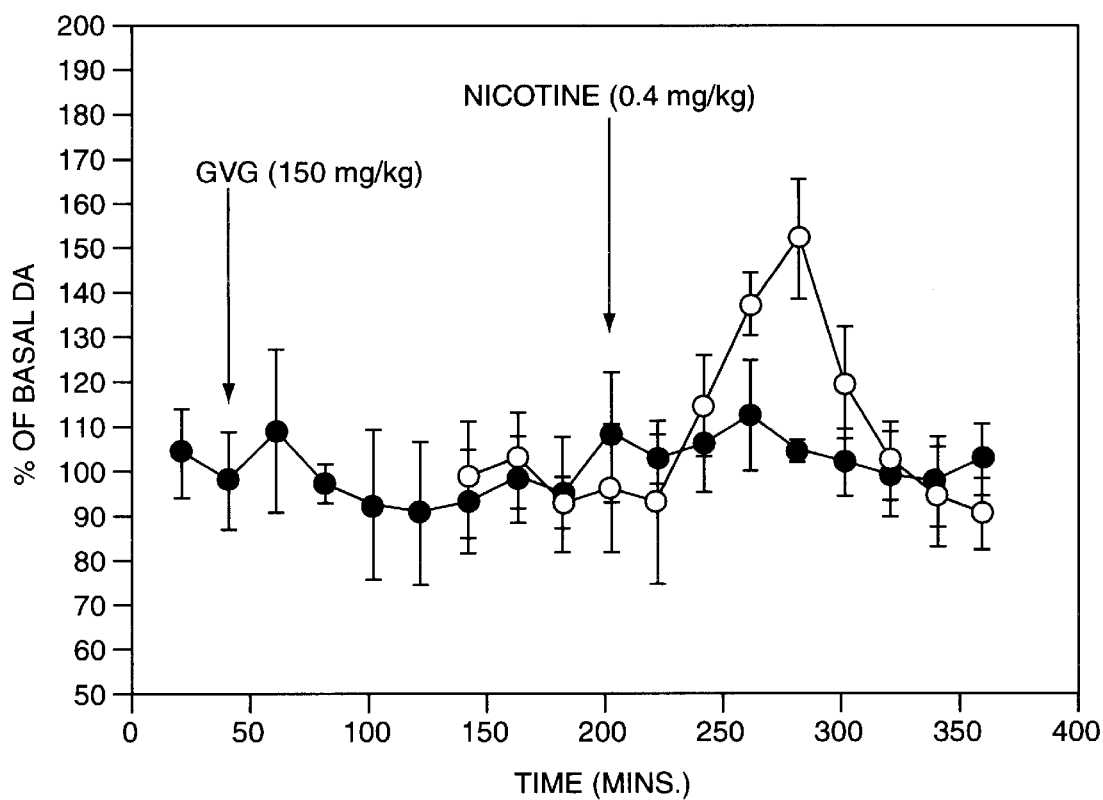
FIG. 4 is a graph illustrating the effects of GVG on nicotine-induced extracellular dopamine.

The results of a similar experiment as the one summarized in Table XII are shown in FIG. 4. FIG. 4 shows that GVG (150 mg/kg) blocks nicotine-induced increases in dopamine concentrations in freely moving rats. The open circles are control animals. The closed circles are from animals treated with GVG 2.5 hours before nicotine.

COMPARATIVE EXAMPLE

Effects of Baclofen on Cocaine Use

Our results obtained in Examples 1, 2 and 3 were consistent with previous studies suggesting that the augmentation of GABAergic function can attenuate the rewarding/reinforcing actions of cocaine and other drugs of abuse. For example, it has been shown that, using the progressive ratio paradigm, the selective $GABA_B$ agonist baclofen produced a dose-dependent decrease in the break points for intravenous (i.v.) administration of cocaine in male Wistar rats, although it did not affect the rate of drug intake. These results suggested that baclofen attenuated the reinforcing effects of cocaine, as a decrease in the break point represents a decrease in the motivation to self-administer cocaine.

It has also been hypothesized that augmentation of $GABA_A$ receptor function cary attenuate cocaine self-administration, as chlordiazepoxide and alprazolam, positive allosteric modulators of the $GABA_A$ receptor complex, decreased the rate of cocaine self-administration. However, this effect is probably related to an increase in the reinforcing value of each unit dose of cocaine, as chlordiazepoxide will increase the break point for cocaine self-administration on a progressive ratio schedule.

The findings with baclofen were reinforced by a recent study from the same laboratory indicating that acute pretreatment of rats with baclofen (1.25–5 mg/kg i.p.) will suppress self-administration of cocaine in a discrete trials paradigm for at least four hours without significantly altering responding for food reinforcement. Microinjection of baclofen into the ventral tegmental area ipsilateral to a stimulating electrode in the lateral hypothalamus of rats produced a rightward shift of the rate-current intensity curve, indicating that baclofen attenuated the rewarding value of the electrical stimulation. However, baclofen did not affect the maximal responding rate for electrical brain stimulation reward or non-reinforced performance levels, suggesting that baclofen's action was not related to alterations in motor performance/dexterity.

A recent study demonstrated that GVG produced a dose-dependent increase in brain stimulation reward thresholds in male F344 rats (Kushner et al., 1997b), without significant effects on motor performance. The decrease in brain stimulation reward thresholds produced by 2.5 and 5mg/kg of intraperitonially administered cocaine was significantly antagonized by 400 mg/kg dose of GVG.

Finally, the CPP response elicited by morphine (8 mg/kg) was significantly attenuated by microinjection of baclofen (0.1–1 nmol) into the ventral tegmental area and this effect was antagonized by the $GABA_B$ antagonist 2-hydroxysaclofen. Thus, despite using different paradigms to assess reward/reinforcement, these studies indicate that activation of $GABA_B$ receptors attenuated the appetitive value of cocaine, morphine and electrical brain stimulation reward.

Previously, it was reported that pretreatment with the GABA-mimetic compound progabide (which augments GABA levels in the brain via its metabolism to GABA), which alone does not produce conditioned place preference or aversion, did not alter the CPP response to 1.5 mg/kg i.p. of amphetamine. However, it is difficult to compare this finding to the present invention as there were differences in rat strains, GABAergic compounds and drugs used to elicit CPP. It should also be noted that progabide was only present for 35 minutes. Since it has been shown that the maximal increase in GABA levels in the brain following systemic progabide occurs four-six hours after injection, GABA levels were not at their maximum during the determination of amphetamine-induced CPP.

Given the evidence suggesting that augmentation of dopaminergic function in the mesolimbic system plays a role in mediating the rewarding/reinforcing effects of cocaine, the abolition of the CPP response to cocaine by GVG may be related to an alteration of dopaminergic activity/function. This hypothesis is supported by our in vivo microdialysis study indicating that acute (300 and 500 mg/kg i.p.) or repeated administration (100, 300, and 500 mg/kg i.p.) of GVG produced a significant dose-dependent decrease in the elevation of extracellular DA levels in the NACC and striatum produced by 20 mg/kg i.p. of cocaine (Dewey, et al., 1998). At the same time, it is unlikely that an alteration in the sensitivity of DA receptors following GVG administration is responsible for its attenuation of cocaine's action, because it is known that the repeated administration of GVG does not alter $D_1$ or $D_2$ receptor sensitivity in the rat striatum. However, no evidence exists regarding GVG's effects on other DA receptors ($D_3$, $D_4$ and $D_5$). Alternatively, it is possible that cocaine could alter $GABA_B$ receptor function, thereby potentially altering the release of neurotransmitters such as DA and this could be antagonized by GVG via elevation of GABA levels and consequent stimulation of $GABA_B$ receptors.

It has also been shown that the repeated administration of cocaine diminishes the effectiveness of presynaptic $GABA_B$ auto and heteroreceptors on lateral septal nucleus neurons in rat brain slices. This may lead to a disinhibtory action and enhanced neurotransmitter release. It is also possible that baclofen could attenuate the action of DA and this would attenuate cocaine's actions. This is indirectly supported by the findings of Lacey et al. (1988), showing that in intracellular recordings from rat substantia nigra zona compacta neurons, the outward currents elicited by DA were occluded by maximal currents produced by baclofen.

Several interpretations of the present results are possible. First, it is possible that GVG could increase the metabolism of cocaine, thereby decreasing the amount which reaches the brain and subsequently diminishing its neurochemical effects and ultimately its behavioral actions. However, this is unlikely as brain levels of $^{11}$C-cocaine were not significantly altered in rats or primates pretreated with GVG (300 mg/kg). Furthermore, cocaine is primarily metabolized by plasma cholinesterases whereas GVG is excreted primarily unchanged in the urine, making a pharmacokinetic interaction unlikely.

It has been reported that drugs which augment GABAergic function can produce sedation and ataxia. Consequently, it is reasonable to postulate that GVG, by producing such adverse behavioral effects, may non-specifically antagonize cocaine's action. However, the results in the present study indicate that GVG does not produce catalepsy or significantly alter locomotor activity, making this hypothesis untenable. Furthermore, the examples discussed above show that GVG does not produce conditioned place aversion, indicating that its antagonism of cocaine's action is not the result of a counterbalancing aversive action. In addition, GVG does not elicit CPP alone, indicating that it is not shifting the preference of animals from the cocaine-paired to the GVG-paired environment.

It has been shown that GVG administration can alter food consumption in rats. Based on this, it is possible that GVG may decrease or attenuate the hedonic value of natural rewards, as well as that elicited by cocaine. However, the present study shows that neither 150 nor 300 mg/kg of GVG alters CPP to food.

Finally, there is evidence indicating that behavior in the conditioned place preference (CPP) paradigm depends upon both the affective and memory-improving properties of the reinforcers under test. Therefore, one might argue that GVG's blockade of the expression and acquisition of cocaine-induced CPP is the result of GVG interfering with the association of cocaine-induced positive incentive value with the appropriate stimuli by interfering with memory. Indeed, it is known that certain drugs which augment GABAergic function can impair memory. However, GVG does not affect place conditioning for food, suggesting that this hypothesis cannot explain GVG's antagonism of cocaine's action in the CPP paradigm.

It has been found that the 112, 150 and 300 mg/kg doses of GVG antagonize the acquisition and expression of cocaine-induced CPP. In contrast, GVG did not elicit a CPP or conditioned place aversion response, indicating that GVG does not antagonize cocaine's action by producing a CPP response alone or by attenuating CPP by producing an aversive effect. Furthermore, GVG did not elicit catalepsy and did not alter the incentive value of food. There is evidence that cocaine-related stimuli or cues will reinstate drug-seeking behavior and craving in detoxified cocaine addicts, thereby leading to relapse. The expression of the CPP to cocaine, determined in the absence of cocaine, is antagonized by GVG. These results indicate that the craving experienced by cocaine addicts can be attenuated by GVG.

Dopaminergic transmission in the NACC has been specifically implicated in the reinforcing properties of cocaine. In the PET studies discussed above, measurements were made in the corpus striatum rather than the NACC. Although DA neurotransmission in the corpus striatum has not been implicated in cocaine reward and reinforcement, the effects of cocaine on extracellular DA levels are qualitatively similar in both areas. In addition, our in vivo microdialysis studies demonstrated the ability of GVG to attenuate cocaine-induced increases in extracellular DA levels to a similar extent in both areas (Dewey, et al., 1997; Morgan and Dewey, 1998).

In the present invention, two different species of rodents and primates were used to conduct imaging and behavioral experiments. However, the mesocorticolimbic DA system is neuroanatomically and neurophysiologically homologous in both species. In addition, the biochemical effects of cocaine on extracellular DA, measured by in vivo microdialysis techniques, are similar in both species, and both rodents and primates readily self-administer cocaine (Morgan, et al., 1998).

Based on the experimental results of the present invention it is submitted that the blockade of the behaviors in the CPP paradigm was due to an attenuation of cocaine's effects on brain DA secondary to the GVG-induced increases in GABAergic inhibition of the mesocorticolimbic DA system.

GVG offers the conceptual advantage of blocking cocaine's incentive motivational and biochemical effects on brain DA by irreversibly inhibiting GABA-T, making the relatively slow de novo synthesis of this enzyme the rate determining step in reversing the inhibition of cocaine's effects. Finally, a recent case report of a cocaine abuser suggests that gabapentin, an anticonvulsant that also potentiates GABAergic transmission via unknown mechanisms, attenuated cocaine withdrawal and craving. Taken together, these data indicate that drugs selectively targeted at the GABAergic system can be beneficial for the treatment of cocaine addiction. More specifically, GVG-induced GABA-T inhibition, which produces an increase in extracellular brain GABA levels, represents an effective drug and novel strategy for the treatment of cocaine addiction.

REFERENCES

The following publications, mentioned in the foregoing specification, are incorporated herein by reference as if set forth in full for all they disclose. Dewey, S. L., Chaurasia, C. S., Chen, C., Volkow, N. D., Clarkson F. A., Porter, S. P., Straughter-Moore, R. M., Alexoff, D. L., Tedeschi, D., Russo, N. B., Fowler, J. S. and Brodie, J. D. GABAergic attenuation of cocaine-induced dopamine release and locomotor activity. Synapse 25: 393–398, 1997.

Dewey, S. L., Smith, G. S., Logan, J., Brodie, J. D., Fowler, J. S., Wolf, A. P. Striatal binding of the PET ligand 11C-raclopride is altered by drugs that modify synaptic dopamine levels. Synapse 13, 350–356, (1993).

Dewey, S. L., Smith, G. S., Logan, J., Brodie, J. D., Yu, D-W., Ferrieri, R. A., King, P. T., MacGregor, R. R., Martin, T. P., Wolf, A. P., Volkow, N. D., Fowler, J. S. GABAergic inhibition of endogenous dopamine release measured in vivo with 11 C-raclopride and positron emission tomography. J. Neuroscience 12, 3773–3780, 1992.

Grant, S. M. and Heel, R. C. Vigabatrin: A review of its pharmacodynamic and pharmacokinetic properties, and therapeutic potential in epilepsy and disorders of motor control. Drugs, 41:889–926, 1991.

Kushner, S. A., Dewey, S. L., Kornetsky, C. Comparison of the effects of vigabatrin on cocaine self-administration and food reinforcement. Soc. Neuro. Abstr. 23: 1942 (1997a)

Kushner, S. A., Dewey, S. L., Kometsky, C. The effects of gamma-vinyl GABA on cocaine-induced lowering of brain-stimulation reward thresholds. Psychopharmacology, 133, 383–388, (1997b).

Lacey, M. G., Mercuri, N. B. and North, A. N. On the potassium conductance increase activated by GABAB and dopamine D2 receptors in rat substantia nigra neurones. J. Physiol. 401: 437–453, 1988.

S. R., Lowinson, J. & Gardner, E. L. Conditioned place preference induced by (9-tetrahydrocannabinol: comparison with cocaine, morphine and food reward. Life Sci. 56, 2073–2080 (1995).

Morgan, A. E., Dewey, S. L. Effects of pharmacologic increases in brain GABA levels on cocaine-induced changes in extracellular dopamine. Synapse 28, 60–65 (1998).

Ring, H. A., Crellin, R., Kirker, S., Reynolds, E. H. Vigabatrin and depression. J. Neurology, Neurosurgery & Psychiatry, 56, 925–928 (1993).

Schlaeper, T. E., Pearlson, G. D., Wong, D. F., Marenco, S., Dannals, R. F. PET study of competition between intravenous cocaine and [11C]-raclopride at dopamine receptors in human subjects. Amer. J. Psychiatry, 154, 1209–1213 (1997).

N. R., Van der Kooy, G. F. & Wenger, J. R. Cholecystokinin produces conditioned place-aversion, not place-preferences, in food-deprived rats: evidence against involvement in satiety. Life Sci. 32, 2087–2093, (1989).

Volkow, N. D., Wang, G. J., Fowler, J. S., Logan, J., Schlyer, D., Hitzemann, R., Liberman, J., Angrist, B., Pappas, N., MacGregor, R., Burr, G., Cooper, T., Wolf, A. P. Imaging endogenous dopamine competition with [11C] raclopride in the human brain. Synapse, 16, 255–262 (1994).

What is claimed is:

1. A method for changing addiction-related behavior of a primate suffering from addiction to cocaine which comprises administering to a primate a composition including gamma vinyl GABA (GVG) in an amount sufficient to diminish, inhibit or eliminate behavior associated with craving of cocaine.

2. The method of claim 1, wherein elimination of behavior associated with craving of cocaine occurs in the absence of a aversive response or appetitive response to GVG.

3. The method of claim 1, wherein said composition contains GVG in an amount of about 100 mg/kg to about 300 mg/kg.

4. The method of claim 1, wherein said composition contains GVG in an amount from about 150 mg/kg to about 300 mg/kg.

5. The method of claim 1, wherein said addiction related behavior is conditioned place preference.

6. A method for changing addiction-related behavior of a primate suffering from addiction to cocaine which comprises administering to a primate a composition including gama vinyl GABA (GVG) in an amount sufficient to attenuate the rewarding/incentive effects of cocaine, in the absence of altering rewarding/incentive effects of food in said primate.

7. The method of claim 6, wherein the rewarding/incentive effects of cocaine is attenuated in the absence of an alteration in the locomotor function of said primate.

* * * * *